(12) United States Patent  (10) Patent No.: US 6,530,896 B1
Elliott  (45) Date of Patent: *Mar. 11, 2003

(54) APPARATUS AND METHOD FOR INTRODUCING AN IMPLANT

(76) Inventor: James B. Elliott, 2108 Paso Verde Dr., Hacienda Heights, CA (US) 91745-4948

(*) Notice: Subject to any disclaimer, the term of this patent is extended or adjusted under 35 U.S.C. 154(b) by 0 days.

This patent is subject to a terminal disclaimer.

(21) Appl. No.: 09/624,565
(22) Filed: Jul. 24, 2000

Related U.S. Application Data

(60) Continuation-in-part of application No. 09/323,307, filed on Jun. 1, 1999, now abandoned, which is a continuation of application No. 09/034,533, filed on Mar. 3, 1998, now Pat. No. 5,908,404, which is a division of application No. 08/645,101, filed on May 13, 1996, now Pat. No. 5,827,293.

(51) Int. Cl.⁷ ............................................. A61M 31/00
(52) U.S. Cl. ........................................................ 604/60
(58) Field of Search .............................. 604/57, 58, 59, 604/60, 61, 62, 63, 14, 15, 16, 311, 187, 104; 606/107

(56) References Cited

U.S. PATENT DOCUMENTS

| 2,513,014 A | 6/1950 | Fields | 128/217 |
|---|---|---|---|
| 3,744,493 A | 7/1973 | Booher et al. | 128/217 |
| 4,086,914 A | 5/1978 | Moore | 128/1.2 |
| 4,361,150 A * | 11/1982 | Voss | 128/263 |
| 4,601,699 A | 7/1986 | Crain | 604/64 |
| 4,657,421 A | 4/1987 | Lin | 401/57 |
| 4,661,098 A | 4/1987 | Bekkering et al. | 604/135 |
| 4,685,904 A | 8/1987 | Krebs | 604/164 |
| 4,863,439 A | 9/1989 | Sanderson | 604/264 |
| 4,966,478 A | 10/1990 | Kuo | 401/57 |
| 4,994,028 A | 2/1991 | Leonard et al. | 604/60 |
| 5,019,053 A | 5/1991 | Hoffman et al. | 604/220 |
| 5,120,316 A | 6/1992 | Morales et al. | 604/148 |
| 5,123,905 A * | 6/1992 | Kelman | 606/107 |
| 5,273,532 A | 12/1993 | Niezink et al. | 604/62 |

* cited by examiner

Primary Examiner—Anhtuan T. Nguyen
Assistant Examiner—Ann Y. Lam
(74) Attorney, Agent, or Firm—Christie, Parker & Hale, LLP

(57) ABSTRACT

An apparatus for introducing an implant into tissue is provided. The apparatus comprises a cartridge having proximal and distal ends, inner and outer surfaces, and a central bore extending therethrough having proximal and distal ends. An implant having proximal and distal ends is within the central bore. A piston is provided proximal to the implant and slidably maintained within the bore, whereby, during operation, the piston moves distally through the bore and urges the implant distally through the bore. The distal end of the cartridge includes a pressure-activated tip section enclosing the distal end of the bore. The bore is enclosed such that sterility of the implant within the bore can be maintained until the implant is released from the cartridge into the patient.

41 Claims, 11 Drawing Sheets

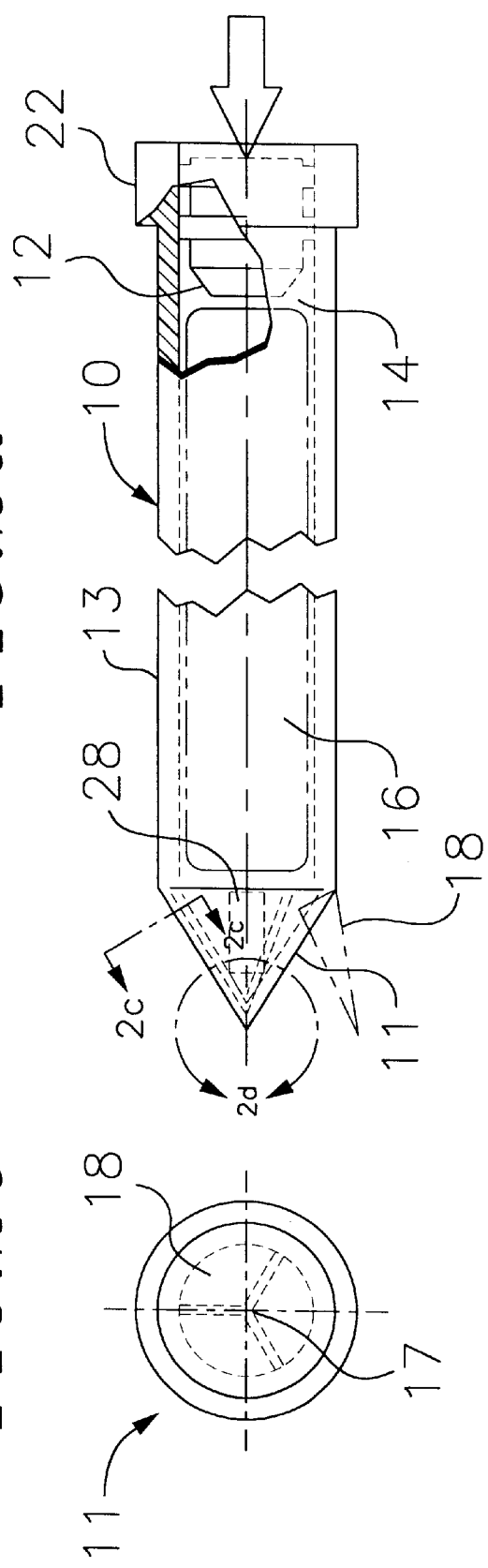
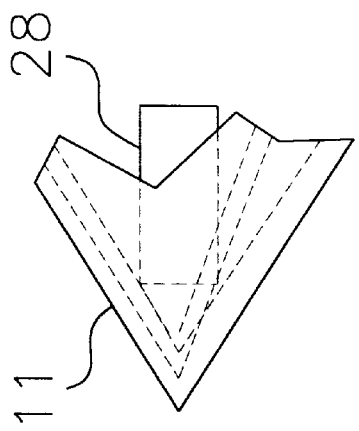
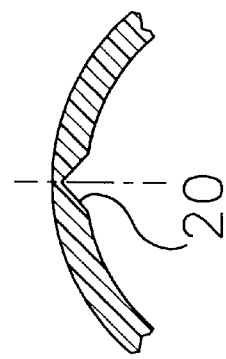

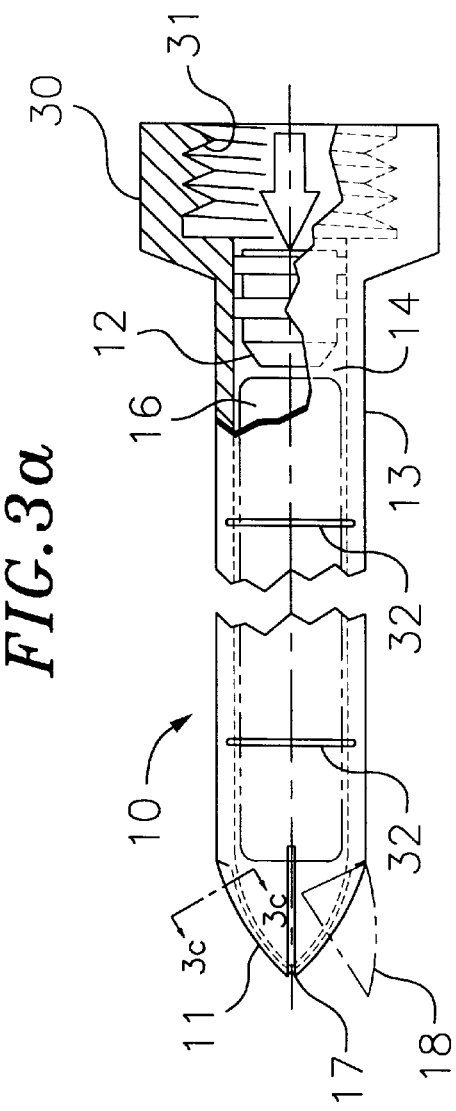
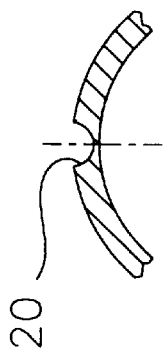
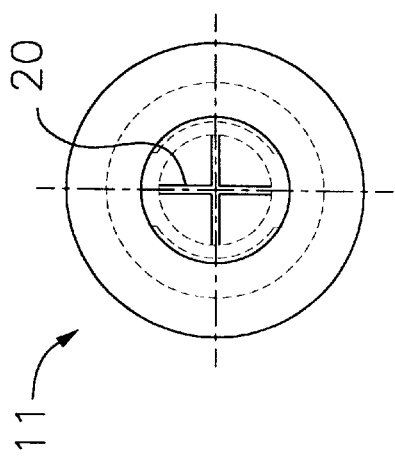
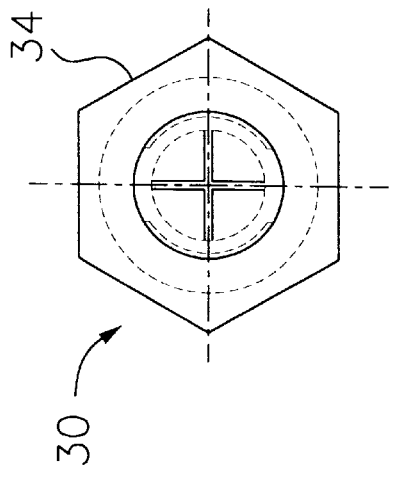

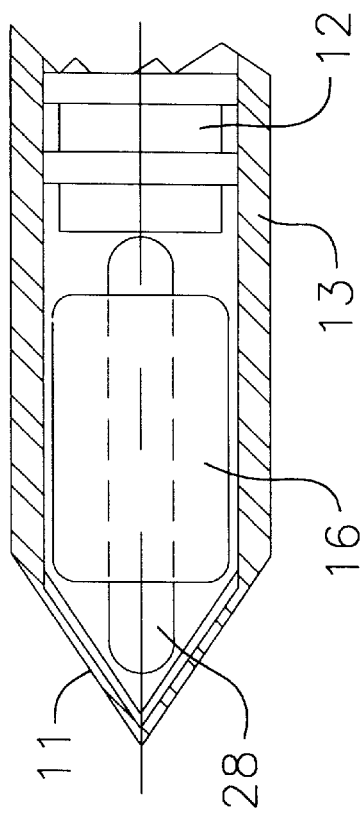
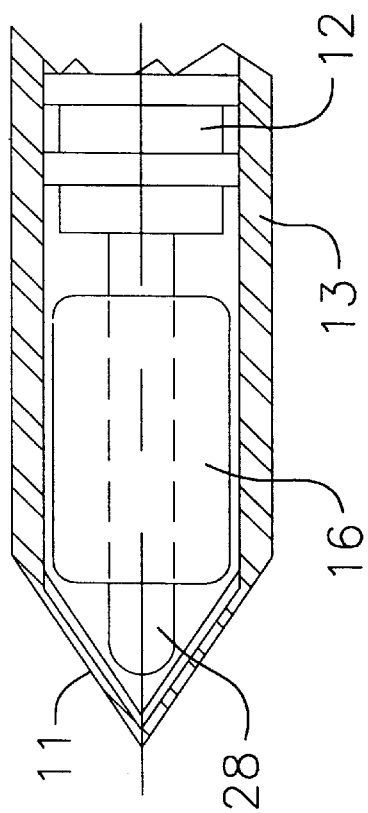

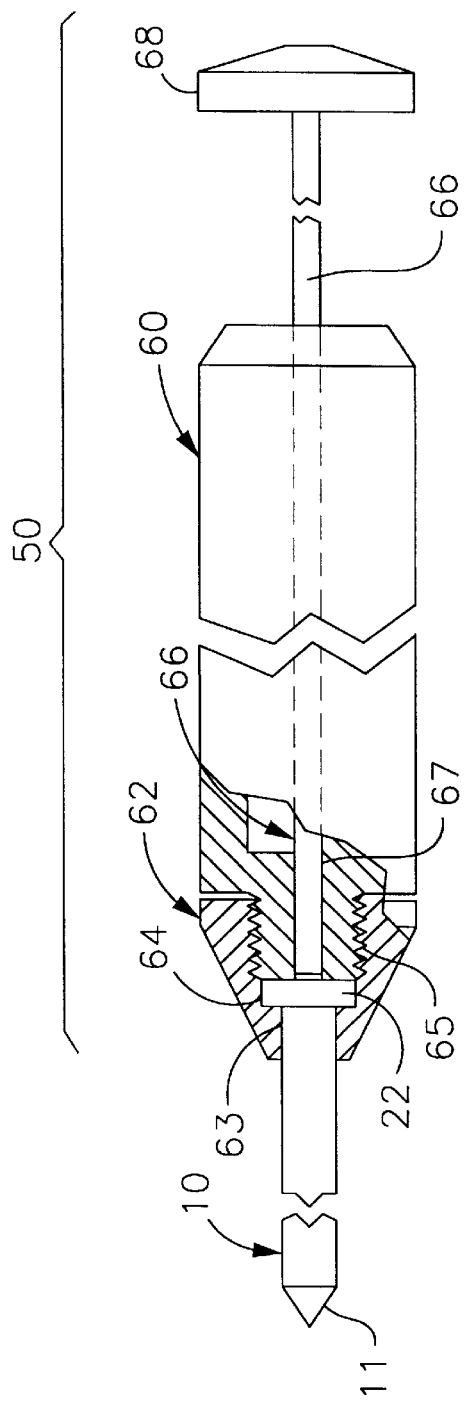
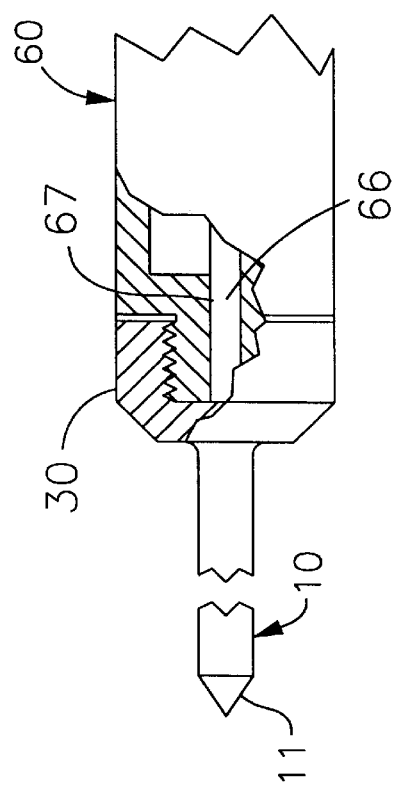
FIG.7a
FIG.7b

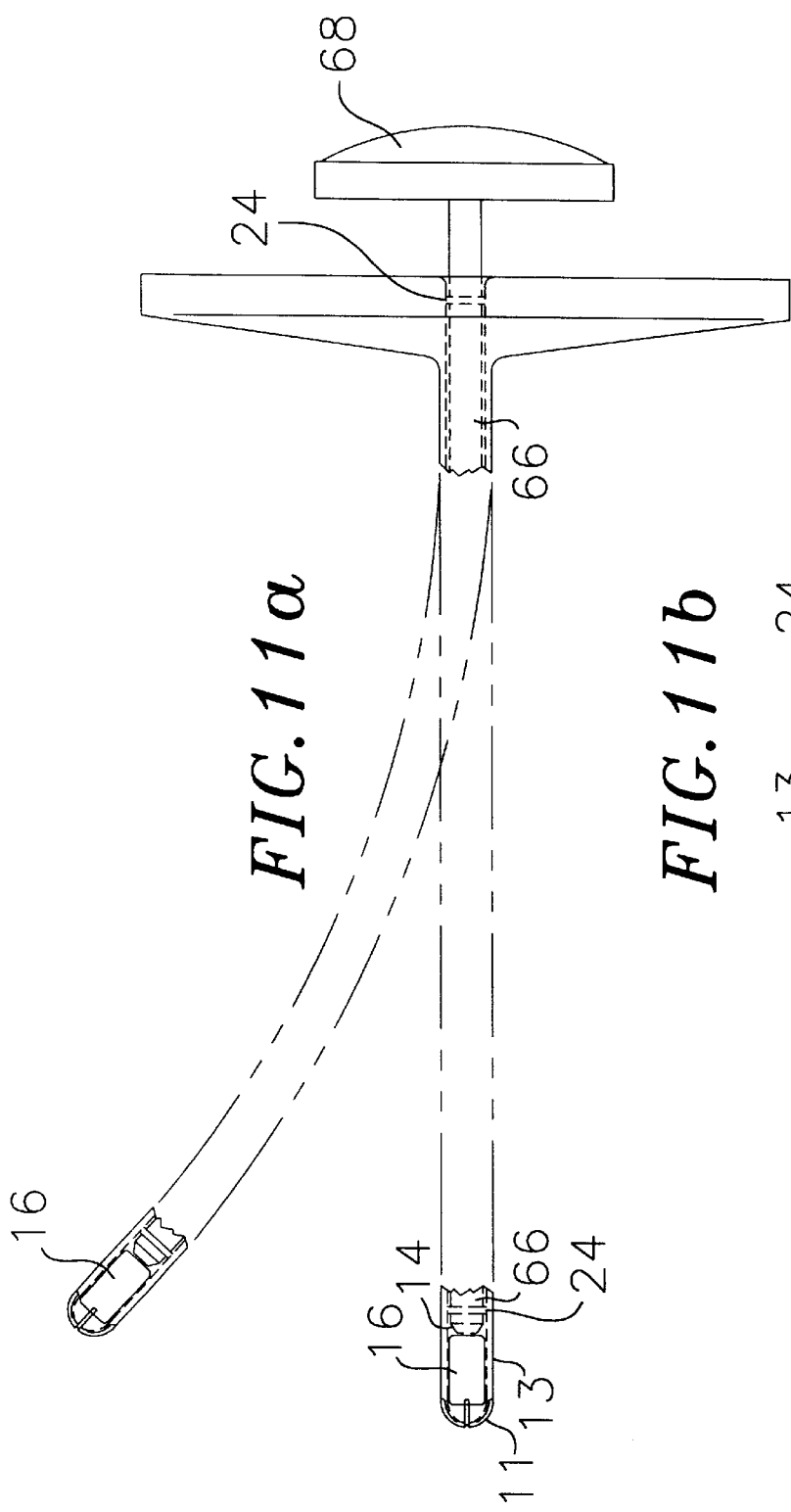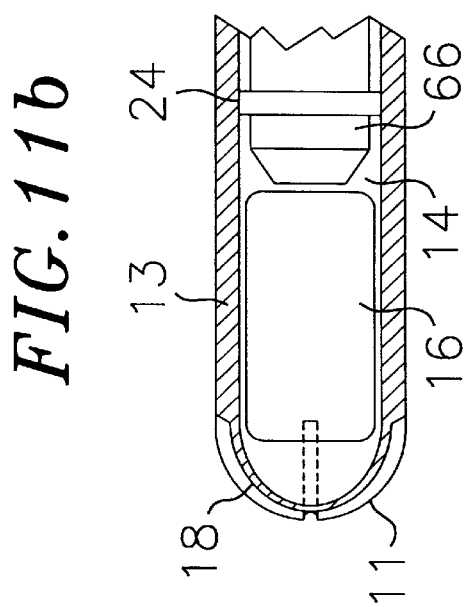
FIG. 11a
FIG. 11b

APPARATUS AND METHOD FOR INTRODUCING AN IMPLANT

CROSS-REFERENCE TO RELATED APPLICATIONS

This application is a continuation-in-part of U.S. application Ser. No. 09/323,307 now abandoned, filed Jun. 1, 1999, which is a continuation of U.S. application Ser. No. 09/034,533, filed Mar. 3, 1998, now U.S. Pat. No. 5,908,404, which is a divisional of U.S. application Ser. No. 08/645,101, filed May 13, 1996, now U.S. Pat. No. 5,827,293, the entire disclosures of which are incorporated herein by reference.

FIELD OF THE INVENTION

The present invention relates generally to the field of inserting inert or active implants in humans and other animals.

BACKGROUND

Application of medicaments to tissue sites over an extended period of time has become possible with the use of timed release implants (TRI) which are inserted subcutaneously and provide release of the medicament included in the implant over a significant period of time. Use of TRIs in the contraceptive field and for administration of insulin and other drugs for control of diabetes and other chronic diseases are becoming conventionally accepted means for medication delivery. Modern genetic engineering is increasingly leading to cures of a variety of diseases by replacement of missing body chemistry. The TRI provides a convenient, medically efficient and cost-effective method of introducing such drugs to a tissue site.

TRIs and similar devices are currently implanted surgically or using insertion devices having large-bore needles through which the encapsulated implant is inserted. Such devices typically require high-cost sterilizable components due to the size of the implants themselves. Use of a large-bore needle of the type necessary to pass an implant can cause serious trauma through coring where the hollow needle actually cuts out a plug of tissue when inserted. In order to prevent coring, the use of a stylette or other means to block the needle bore during insertion is required which adds to the complexity of the insertion device, its associated cost and sterilization requirements. Additionally, a determination of the depth of insertion for the implanting site and accurate placement of the implant are required. Conventional beveled needles, particularly of large bore, have a tendency to slice through tissue at an angle to the needle axis, thereby making control of needle insertion and consequent accuracy of placement of the implant, difficult. Alternatively, placement of implants is accomplished at surgically accessed sites by manipulation with forceps or other common surgical tools. These procedures take considerable time to perform, result in greater trauma to the tissue and require extreme care in avoiding contamination of the implant during extraction from packaging and handling. A determination of the depth of the implant typically requires a special gauge, or is measured by approximating the depth of insertion through measurement of the exposed portion of the needle. Either process is typically time-consuming and subject to error or accidental contamination of the implantation site.

It is therefore desirable that an implant insertion device comprise a disposable portion which maintains the implant in a sterile environment and is itself easy to maintain in a sterile condition prior to use. It is further desirable that the implant insertion device include a symmetrical non-coring piercing device with integrated insertion depth measurement to allow accurate insertion of an implant through an existing orifice, subdurally, subcutaneously or in an intramuscular location as appropriate for the particular implant device.

SUMMARY OF THE INVENTION

The present invention provides an apparatus and method for delivering a variety of implants, particularly under non-clinical (and non-sterile) environments, to tissue. Prior art devices, as discussed above, require the user to insert the implant into the insertion device immediately prior to use during a surgical procedure, which often requires considerable training so that a fragile implant is not damaged during placement in the insertion device. Moreover, sterility must be maintained during the handling and placement of the implant. The inventive apparatus and method, in contrast, are simple and safe and can be used by minimally-skilled and minimally-trained users, while maintaining the sterility of the implant.

The method and apparatus of the invention are useful for virtually any type of small implant, as described in more detail below. The implant can be inserted as is known in the art, such as into surgically-accessed vessels or tissue, through any natural body orifice, or by subcutaneous introduction. In the case of subcutaneous implanting, the delivery system can be self-introducing, without any surgical preparation of the introduction site.

The implant is sealed in a sterile cartridge until the moment of release at the target site. An implant can be placed with confidence of sterility, even in non-surgical environments. Because of inherent characteristics of the technology, less invasive implanting procedures are feasible, reducing tissue trauma and infection risk. For subcutaneous implanting procedures, only simple local anesthesia is needed. Further, healthcare workers with minimal training can safely administer subcutaneous implanting under primitive field conditions. The skill level required is comparable to that required for administering hypodermic inoculations.

In one embodiment, the invention is directed to an apparatus for introducing an implant or plurality of implants into tissue, which can be human tissue or tissue of another animal, living or dead. The apparatus comprises a cartridge having proximal and distal ends, inner and outer surfaces, and a central bore extending therethrough having proximal and distal ends. An implant, or plurality of implants, having proximal and distal ends is within the central bore. A piston is provided proximal to the implant and slidably maintained within the bore. During operation, the piston moves distally through the bore and urges the implant(s) distally through the bore. The piston can urge the implant(s) directly, i.e., be in direct contact with an implant, or indirectly, i.e., with an intermediate device positioned between the piston and the implant(s). An openable, an preferably pressure-activated, tip section is provided at the distal end of the cartridge enclosing the distal end of the bore and having inner and outer surfaces. The bore is enclosed such that sterility of the implant(s) within the bore can be maintained until released from the cartridge into tissue.

In a preferred embodiment, the piston of the apparatus is in contact with and maintains a seal with the inner surface of the cartridge. The tip section is segmented or frangible into a plurality of segments under pressure from the distal end of the implant and includes means for inducing stress fracture of the tip to create the plurality of frangible segments. The apparatus further comprises reinforcement means extending from the cartridge body to the segments of the tip section to prevent separation of the segments from the tip section subsequent to fracture.

In another embodiment, the invention is directed to a system for inserting an implant, or plurality of implants, into a tissue site. The system comprises an apparatus as set forth above and an insertion tool for urging the piston distally through the bore. The insertion tool preferably comprises means for fixedly or removably attaching the tool to the cartridge and a plunger or other means for distally moving the piston.

In another embodiment, the invention is directed to a method for introducing an implant, or plurality of implants, into a tissue site. The method comprises providing an apparatus as described above. At least a portion of the tip section is inserted into the tissue. The piston is moved distally through the bore, thereby urging the implant(s) distally through the bore. Pressure is exerted on the tip section with the implant(s) to permit the implant(s) to open the tip section and exit the bore. The pressure can be exerted by the implant(s) directly, i.e., with an implant in direct contact with the inner surface of the tip section, or indirectly, whereby an assist plug or other device is in contact with the inner surface of the tip section and an implant so that distal movement of the implant(s) results in distal movement of the assist plug, urging the assist plug against the tip section.

DESCRIPTION OF THE DRAWINGS

These and other features of the advantages of the present invention will be better understood by reference to the following detailed description when considered in conjunction with the accompanying drawings wherein:

FIG. 1b is a forward end view of the distal tip of the embodiment shown in FIG. 1a;

FIG. 1c is a section view along line 1c—1c of FIG. 1a;

FIG. 2a is a partial section side view of a cartridge incorporating a second embodiment of the invention;

FIG. 2b is a front-end view of the distal view of the tip of the cartridge shown in FIG. 2a;

FIG. 2c is a sectional view along line 2c—2c of FIG. 2a;

FIG. 2d is a detailed view showing assist plug for fracturing of the distal tip;

FIG. 3a is a partial section side view of a cartridge incorporating a third embodiment of the invention;

FIG. 3b is a front-end view of the distal tip of the cartridge shown in FIG. 3a;

FIG. 3c is a sectional view along 3c—3c of FIG. 3a;

FIG. 3d is an end view showing an alternate embodiment of the retention hub for the cartridge shown in FIGS. 3a and 3b;

FIG. 6a is a side view of a cartridge containing a tubular implant and having an assist plug that extends through the tubular implant;

FIG. 6b is a side view of a cartridge containing a tubular implant and having an assist plug that extends through the tubular implant and that is attached to the piston;

FIG. 7a is a partial sectional side view of an insertion tool for cartridges incorporating the present invention;

FIG. 7b is a partial view of a second embodiment of the insertion tool of FIG. 7a employing an alternative means for attachment of the cartridge;

FIG. 11a is a partial sectional side view of an alternative integral insertion device suitable for vascular implant(s) or other long-reach delivery; and FIG. 11b is an enlarged sectional side view of the distal end of the insertion device of FIG. 11a.

DETAILED DESCRIPTION

Figure 1A:
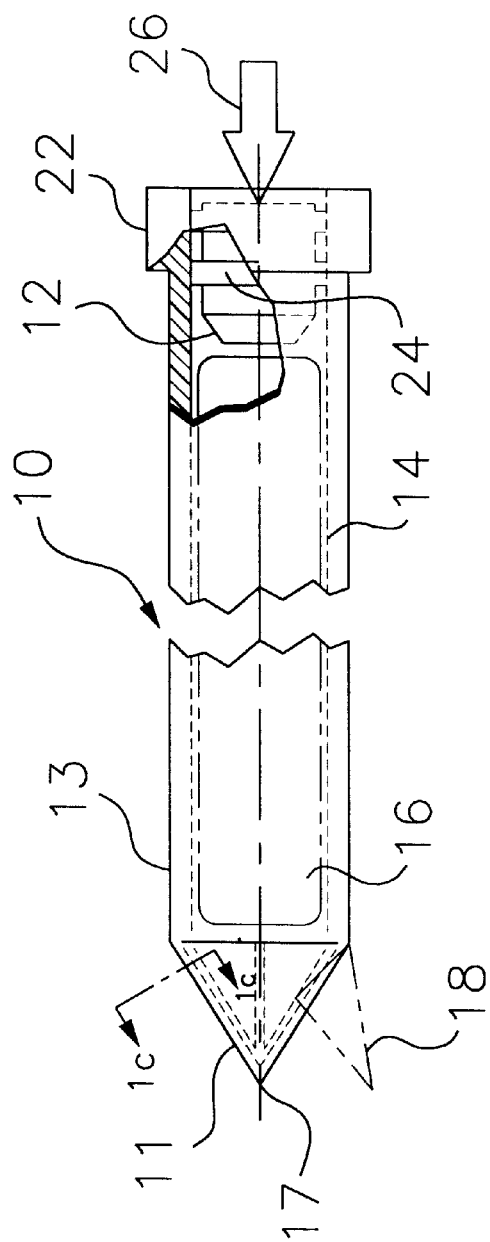
FIG. 1a is a partially sectioned side view of a cartridge incorporating the present invention.

One embodiment of an implant insertion device constructed in accordance with the present invention is shown in FIGS. 1 to 4. The insertion device comprises a cartridge 10, having proximal and distal ends, a tip section 11 at the distal end of the cartridge 10, and a piston 12 at the proximal end of the cartridge 10.

The cartridge 10 comprises a substantially cylindrical body 13 and an internal bore 14 extending therethrough. One or more implants 16 are contained within the bore 14. The cross-sectional area of the body 13 can be any other suitable shape, for example, oval, square, rectangular, hexagonal, or triangular. The cross-sectional area of the bore 14 can also be of any suitable shape, and is preferably a shape similar to that of the implant(s) 16 to be contained within the cartridge 10. The inner diameter of the bore 14 preferably ranges from about 0.3 mm to about 3.0 mm, depending on the implant(s) to be used with the device.

The embodiments of the invention shown in the drawings may be constructed of either metallic or non-metallic materials, and preferably are molded and/or machined from surgical purity plastic polymers, such as polypropylene, polystyrene and acrylic polymers. Standard injection molding processes for medical components are well known in the art and will not be described in detail herein. If desired, the piston 12 may comprise, in whole or in part, a gas-permeable biobarrier material, such as open-cell expanded foam, fused microfiber Teflon, or polypropylene to allow ethylene oxide gas sterilization of the implant(s).

The tip section 11 is located at the distal end of the cartridge 10. The tip section 11 is a pressure-activated openable tip and is generally cone-shaped, having a generally pointed distal end 17 and comprising four segments 18, which are frangibly joined at their edges. The pointed distal end 17 of the tip section 11 allows the insertion device to penetrate tissue to an appropriate depth for exact placement of the implant(s) 16. As would be recognized by one skilled in the art, the number of segments 18 can vary as desired.

The tip section 11 is integral with, i.e., permanently attached to, the cartridge 10. Alternatively, the tip section 11 can be removable. For example, the proximal end of the tip section and the distal end of the cartridge can contain threads, allowing the tip section to screw into or onto the cartridge.

Figure 1B:
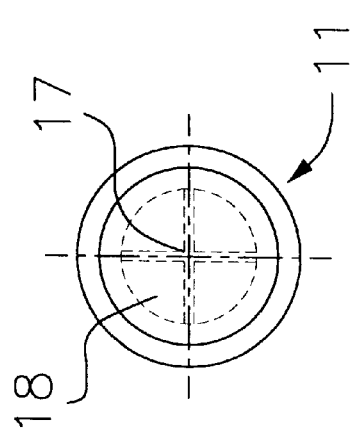
Figure 1C:
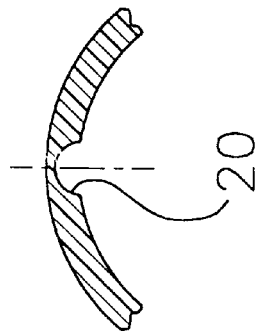

As shown in FIGS. 1b and 1c, the frangible segments 18 of the tip section 11 are defined by circular cross-section grooves 20 internal to the tip section. The number of frangible segments 18 is not critical and can be varied as desired. The grooves 20 define high-stress fracture lines in the tip section 11, and can be of any other suitable shape, such as the v-shaped grooves shown in FIG. 2c. Alternatively, the grooves 20 can be formed external to the tip section 11, such as shown in FIG. 3c. The grooves 20 are imparted to the tip section 11 by any known technique, for example, through scoring or machining of the interior or exterior of the tip section subsequent to molding or by appropriately placed splines on the molding mandrel for the insertion device. In a preferred embodiment, the grooves 20 are formed directly into the tip section 11 when the tip section is molded by using an appropriately designed mold. Urging of an implant 16 against the interior of the tip section 11, as described in more detail below, causes the tip section 11 to fracture along the grooves 20 into the frangible segments 18 shown in phantom in FIG. 1a, allowing the implant(s) 16 to open the tip section and emerge from the cartridge 10.

A piston 12 is located at the proximal end of the cartridge 10 and extends into the distal end of the internal bore 14 of the cartridge. The piston 12 which generally has the same cross-sectional shape as the internal bore 14, may be for the most part slightly smaller, but includes at least one generally annular sealing portion which is deformably larger than the internal bore 14. The piston 12 is of any length suitable to the specific implanting use. In the depicted embodiment, the piston 12 has a circular cross-sectional shape. The piston 12 has one or more ribs 24 around its circumference. The ribs 24 create an interference fit between the piston 12 and the wall of the internal bore 14, creating a seal at the proximal end of the internal bore 14. The seal created by the ribs 24 on the piston 12 permits the user to maintain the sterility of the internal bore 14, while still permitting the piston 12 to slide within the internal bore. The piston 12, including the ribs 24, is made of a material capable of maintaining the interference fit. Nonlimiting examples of suitable materials for the piston include latex rubber, low density polyethylene, polybutadiene and similar elastomeric polymers. Other piston 12 designs can alternatively be used, so long as the piston is capable of maintaining a seal with the wall of the internal bore 14 while still being able to slide within the bore.

In the embodiment illustrated in FIG. 1a, the piston 12 is in the form of a closure plug. The proximal end of the cartridge 10 terminates in a retention shoulder 22. The retention shoulder 22 extends from the body 13 of the cartridge 10 to allow a convenient handling site for the user, and is further adapted to retain the cartridge in an insertion tool, described in more detail below, that can be temporarily attached to the cartridge 10. The piston 12 is engaged by a plunger, rod or the like in the insertion tool, which exerts a force in the direction of arrow 26, urging the piston against the implant(s) 16.

FIGS. 2a, 2b, 2c and 2d show another embodiment of the present invention having a general configuration and function similar to that disclosed in FIGS. 1a, 1b and 1c. The tip section 11 has three frangible segments 18, as best seen in FIGS. 2b and 2c, defined by V-shaped grooves 20, which are internal to the tip section 11. Additionally, as disclosed in FIG. 2d, this embodiment employs an assist plug 28 having proximal and distal ends and a diameter smaller than that of the implant(s) 16. The assist plug 28 is inserted into the cartridge 10 prior to the implant(s) 16. The proximal end of the assist plug 28 contacts the distal end of an implant 16, and the distal end of the assist plug contacts the interior of the tip section 11. The reduced diameter of the assist plug 28 bears on a smaller relative area of the tip section 11, thereby increasing the stress on the tip section by concentrating the force from the implant(s) 16 for initial fracture of the frangible segments of the tip, thereby enhancing expulsion of the implant(s). The assist plug 28 can be made of any suitable material, for example, the same material as the implant(s) or a harmless bioresorbable material, such as suture-grade collagen, polylactic polymer, or polyglycolic polymer. Shaping of the assist plug 28 to achieve maximum stress on the tip section 11 through force applied to the assist plug by the implant(s) 16 is desirable.

Another embodiment of the invention is depicted in FIGS. 3a, 3b and 3c. In this embodiment, the proximal end of the cartridge 10 incorporates a retention hub 30 having internal threads 31 for attachment of the cartridge to the insertion tool. The retention hub 30, which is preferably larger than the previously-described retention shoulder 22, is advantageous over the retention shoulder for applications where the cartridge 10 is relatively small so that the user needs a larger grasping area on the cartridge when attaching the cartridge to the insertion tool. FIG. 3d shows an alternate configuration for the retention hub 30 that incorporates hexagonal flats 34 to assist in tightening the threaded connection of the retention hub to the insertion tool using fingers or a wrench. Other commonly known means for providing increased gripping and/or engagement utility for either fingers or tools can also be employed in accordance with the invention.

This embodiment also employs a generally pointed tip section 11 having a curved profile, best seen in FIG. 3a, and external circular cross section grooves 20, best seen in FIGS. 3b and 3c, for creating the fracture lines for the frangible segments 18 of the tip section. Shaping of the external grooves is also advantageous in assisting in separation of epidermal tissues during insertion of the tip and cartridge to a proper depth for the implant.

The body 13 of the cartridge 10 incorporates striations 32 on the exterior surface of the body. The striations 32 are placed at predetermined locations along the body 13 to provide a visual cue for the user to determine depth of penetration of the tip section 11 for appropriate placement of the implant(s) 16. The striations 32 are preferably formed from shallow grooves or other means providing visible yet biocompatible markings, such as laser or chemical etchings or painted lines that will not peel or flake off the device. In an alternative embodiment, visualization of the cartridge within tissue is further enhanced by affixing or imbedding metallic reference markers (not shown) in the cartridge body 13 and/or tip section 11, or alternatively by admixing or applying radiopaque material to the body and/or tip section, in combination with the use of standard surgical fluoroscopy equipment.

Figure 4C:
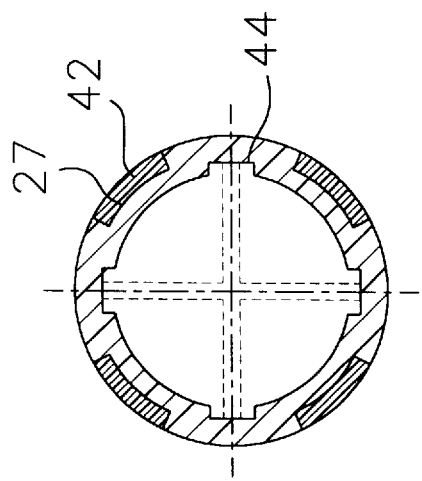
FIG. 4c is a sectional view showing a third embodiment for external reinforcing members for the frangible tip segments.

To assure that the frangible segments 18 of the tip section 11 do not create loose debris when fractured during expulsion of the implant(s) 16, the areas between the frangible segments and the body 13 are reinforced. FIGS. 4a, 4b, 4c and 4d demonstrate alternative embodiments for such reinforcement. FIG. 4a demonstrates the use of embedded reinforcement members 36 integrally molded into the cartridge 10 and extending into the frangible segments 18 and body 13 to reinforce the unfractured interface between the tip section 11 and body.

Figure 4B:
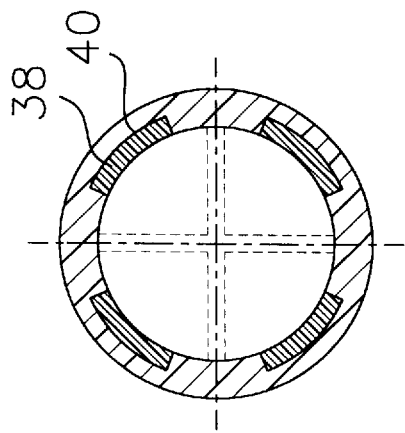
FIG. 4b is a sectional view showing a second embodiment for internal reinforcing members for the frangible tip segments.

FIG. 4b depicts an alternative design employing internal reinforcing members 38 that constitute strips of reinforcement material embedded in internal grooves 40 extending into the tip section 11 and body 13. Bonding of segments of reinforcement strips into premolded grooves, or integral molding of the cartridge over an insert, formed from metal or polymer having high ductility and flexibility, placed in the molding cavity, may be employed for fabrication.

Figure 4D:
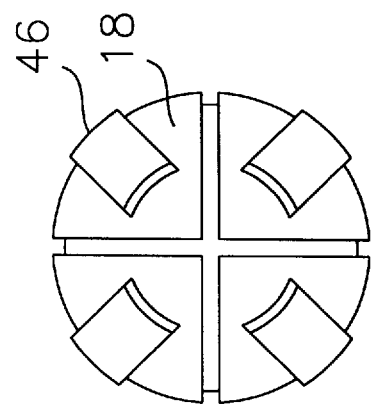
FIG. 4d is a front view showing a fourth embodiment for external reinforcing members for the frangible tip segments.
Figure 4A:
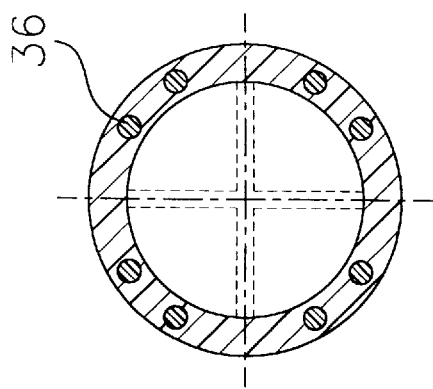
FIG. 4a is a sectional view showing embedded reinforcement members for the frangible tip segments of the cartridge.

FIG. 4c demonstrates an alternative embodiment for reinforcement employing external reinforcing members 42 in grooves 27 extending on the exterior surface of the frangible segments 18 and body 13. As with the internal reinforcing members described above, the external reinforcing members 42 are bonded in premolded grooves 27 in the cartridge 10 or integrally molded into the cartridge by preplacement in the mold cavity. Alternatively, tape strips 46, made, for example, of MYLAR™ or a similar material, are applied by adhesive or other bonding mechanism to the cartridge 10 after molding in the premolded grooves or, with sufficiently thin material, directly to the exterior surface of the tip section 11, as shown in FIG. 4d.

In each of the embodiments for reinforcement previously described, the reinforcing members act as a hinge for the frangible segments 18. Scoring or grooves 44, which are intermediate the reinforcing members, as shown in FIG. 4c, and extend partially into the distal end of the body 13 to enhance fracture line control from the frangible tip segments, are employed in alternative designs to assure integrity of the reinforcing member hinges during fracture of the tip.

Figure 5:
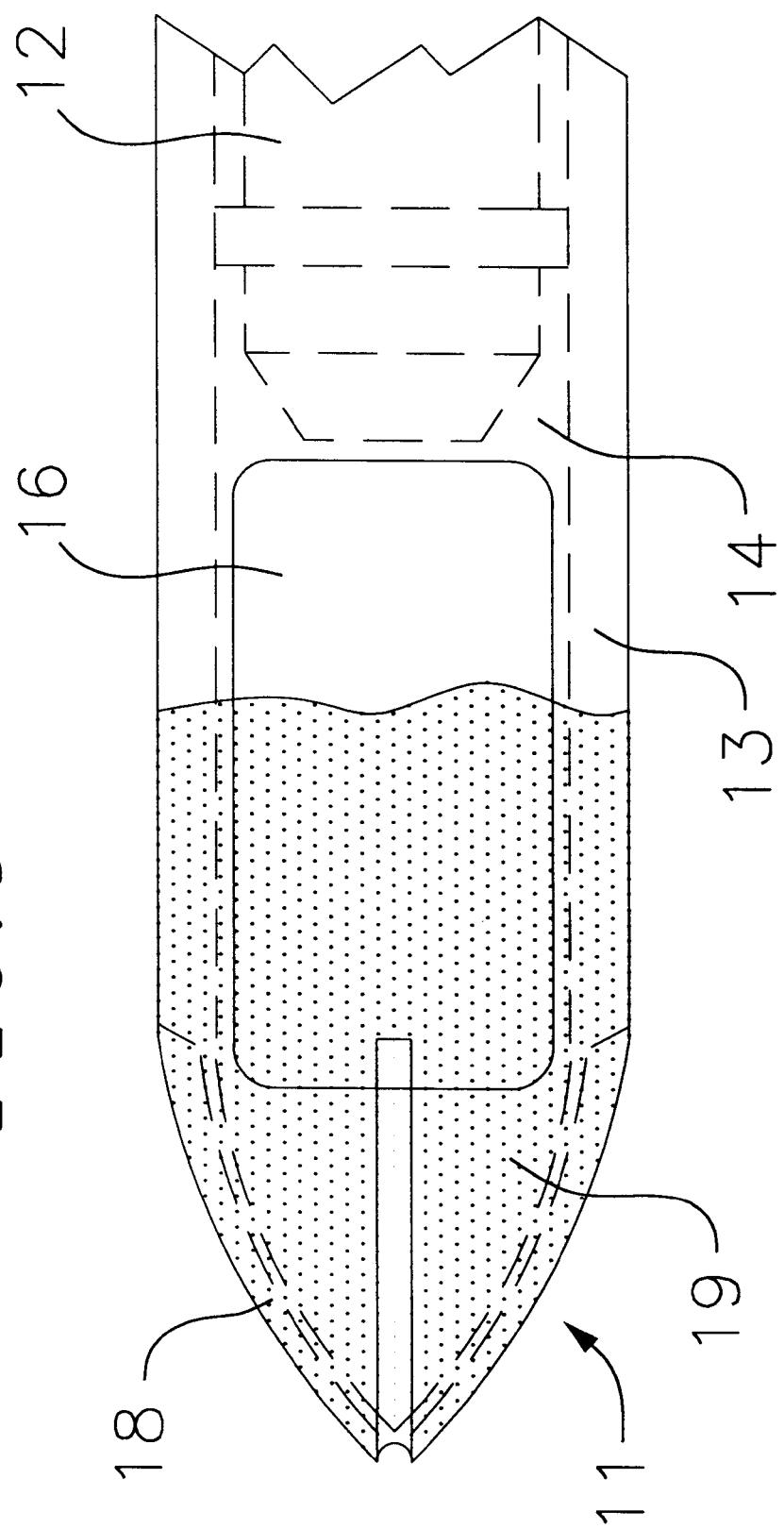
FIG. 5 is a side view of a cartridge having a coating for reinforcing the frangible tip segments and assuring a seal of the cartridge.

An alternative mechanism for reinforcing the frangible segments is depicted in FIG. 5. The tip section 11 is a pressure-activated self-opening tip having a plurality of frangible segments 18, as described above. The junction between the tip section 11 and the cartridge body 13 is covered with a coating or membrane 19. The coating 19 reinforces the junction between the tip section and cartridge body to keep the frangible segments 18 from breaking off the insertion device during a procedure. The coating extends partially or completely over the tip section 11 and can extend along the cartridge body for any desired length. The coating 19 can be applied by any known technique, such as spraying, dipping or painting. FIG. 5 shows the coating 19 applied to the outer surface of the cartridge and tip section, although it can also be applied to the inner surface of the cartridge and tip section. Preferably the coating is formed from a biocompatible epoxy (such as EPO-TEK 301, commercially available from Intertronics, Kidlington, England, or PERMABOND 4E98, commercially available from Permabond, Englewood, N.J.), urethane, wax, or similar compounds used in hot-melt adhesives. In the embodiment depicted in FIG. 5, the tip segments 18 enclose, but do not necessarily seal the distal end of the cartridge 10; however, the coating or membrane 19 bridges any gaps between the segments 18, providing the assurance of a seal, until tearing open at the moment of release of the implant(s).

In another embodiment, as shown in FIG. 6a, the insertion device is used with a tubular implant 16. An assist plug 28 is provided that extends through one or more tubular implants. The assist plug would remain in the recipient's body with the implant(s), as described above with reference to FIG. 2d. Alternatively, as shown in FIG. 6b, the proximal end of the assist plug 28 is fixedly attached to the distal end of the piston 12 (closure plug). In this alternative embodiment, as the piston urges the assist plug distally, the assist plug pushes open the tip section and carries the tubular implant(s) out of the cartridge as it continues forward. The assist plug is prevented from completely exiting the cartridge by its attachment to the piston so that only the implant(s) is left in the recipient.

An insertion tool 50 for use with the insertion cartridge 10 of the present invention is shown in FIGS. 7a and 7b. The insertion tool 50 of FIG. 7a comprises a handle 60 that incorporates a cartridge attachment portion 62 for receiving the cartridge 10. The cartridge attachment portion 62 includes a cylindrical aperture 63 through which the body 13 of the cartridge 10 is received and a counterbore 64 that receives and retains the retention shoulder 22 of the cartridge, such as the cartridge shown in FIG. 1a. In the depicted embodiment, the cartridge attachment portion 62 incorporates an internal thread that is capable of mating to a threaded nipple 65 on the handle 60. Any other method of attaching the cartridge attachment portion 62 to the handle 60 could also be used.

A plunger is provided comprising a plunger rod 66 having a thumb knob 68 at its proximal end. The plunger rod 66 extends through a bore 67 in the handle 60 and is aligned with the proximal end of the cartridge 10 to enable engagement of the piston 12. The thumb knob 68 extends outside the proximal end of the handle 60 and has a size greater than that of the bore 67 to prevent the plunger rod 66 from extending too far distally and pushing the proximal end of the piston 12 out the distal end of the cartridge 10. Any other mechanism for limiting distal movement of the plunger rod 66, and thus the piston 12, could also be provided. This embodiment is particularly suited for single-handed use, wherein the thumb knob 68 is engaged by the user's thumb while the handle 60 of the insertion tool 50 is grasped in the user's fingers and the palm of the user's hand. Alternatives providing mechanical advantage through ratchet or spring loaded actuators including travel limitation devices for the rod to assure proper dispensing of the individual implant(s) while maintaining the piston (closure plug) within the cartridge are employed in tools 50 for applications in which consecutive multiple implant releases can be provided. An alternative embodiment (not shown) with standard finger grips and thumb pad for depressing of the plunger rod 66 is employed as an alternative to enable one-handed manipulation of insertion tool 50 similar to the configuration and use of a common hypodermic syringe. Those skilled in the art will recognize alternative approaches for urging the plunger rod through the insertion tool to engage the piston including spring loaded actuation arrangements such as that found in mechanical pencils which are particularly suited for insertion of multiple implants from a single cartridge.

The insertion tool shown in FIG. 7a is adapted in alternative embodiments for direct external loading of the cartridge into the tool 50. For example, a slot and interconnecting aperture (not shown) can be provided in a sidewall of the handle 60 and sized to receive the retention shoulder 22 to retain the cartridge 10 and resist longitudinal movement of the cartridge within the insertion tool. A rotating barrel to close the aperture and slot subsequent to insertion of the cartridge may also be employed.

FIG. 7b discloses a second embodiment for the insertion tool 50 employed with the alternative embodiment for the insertion cartridge 10 shown in FIG. 3a which employs a retention hub 30 having internal mating threads. The retention hub 30 on the cartridge eliminates the necessity for the separate cartridge attachment portion 62 of the embodiment of FIG. 7a and provides direct attachment of the cartridge 10 to the insertion tool handle 60 with alignment of the plunger rod 66 for engagement of the piston 12. Operation of this alternative insertion tool is substantially identical to that described for the insertion tool disclosed in FIG. 7a.

In an alternative embodiment similar to the embodiment depicted in FIG. 7a, the cartridge attachment portion 62 has a threaded tip (not shown) for insertion into a cartridge retention hub, such as that of the embodiment shown in FIG. 3a, thereby accommodating various size cartridges 10 on a single size handle 60 in a manner similar to FIG. 7b.

The loading of one or more implants in the cartridge is accomplished in a standard clean room manufacturing environment, which may be automated based on the configuration of the embodiments of the invention disclosed in the drawings, with installation of the implant(s) and assist plug, when employed, followed by closure of the cartridge with the piston (closure plug). The cartridge, which preferably is single-use cartridge, is sterilized by standard autoclave, radiation or ethylene oxide gas sterilization processes. The one or more implants are contained in the cartridge during sterilization. Sterility of the cartridge and implant(s) is maintained prior to use using standard biobarrier packaging commonly available in the health care and medical industries for protecting sterile integrity of medical devices.

The insertion tool is preferably a multi-use device that can be used with different cartridges for different implantation procedures. Sterility of the insertion tool during each use is enhanced through the use of a prophylactic covering, either preattached to the cartridge assembly or separably mountable in a form such as that disclosed in U.S. Pat. No. 5,228,851 to Burton, the disclosure of which is incorporated herein by reference. While the Burton device is disclosed with regard to dental tools, application of such a covering to an insertion apparatus as disclosed herein would reduce any requirements for sterilizing the insertion tool employed with the present invention.

The configuration of the insertion tool of the present invention is particularly suited for packaging the cartridge in standard sterilizable blister pack or similar forms having an access tab end adjacent the proximal end of the cartridge. Handling of the cartridge is accomplished by grasping the retention shoulder or retention hub, thereby avoiding contamination of the remainder of the cartridge during attachment to the insertion tool. Alternatively, after the user partially opens a portion of the sterile packaging covering the proximal end of the cartridge, the user grasps the cartridge distal end through the thin flexible sterile packaging and attaches it to the insertion tool, at which time the remaining sterile packaging material is slipped off without contaminating any cartridge surfaces.

To employ the cartridge for insertion of one or more implants using the insertion tool configuration of FIG. 7a and FIG. 7b, the user removes the cartridge from its packaging by one of the methods described above, thereby maintaining the sterile condition of the tip and body of the cartridge. The cartridge is affixed to the previously cleaned and/or sterilized re-useable insertion tool. After preparation of the insertion site as necessary, the user manipulates the insertion tool to enter the tissue with the cartridge tip, preferably using the markings on the cartridge body to determine proper depth of insertion. The thumb knob of the plunger is then depressed to urge the plunger rod against the piston, which in turn urges the implant(s) against the interior of the tip of the cartridge, thereby fracturing the frangible tip and allowing the implant(s) to emerge from the cartridge. The plunger rod is sized to provide contact of the plunger with the handle body upon complete insertion of the implant (s) or, alternatively, is marked to allow visual confirmation of proper depression depth. The insertion tool and cartridge are alternatively employed to introduce one or more implants or devices into a body cavity, vessel or organ through a natural orifice or in conjunction with a surgical procedure.

Upon completion of the insertion of the implant(s), the user removes the cartridge from the implanting site by withdrawing the insertion tool. The cartridge is disengaged from the insertion tool and properly discarded. The insertion tool is then reusable with additional implant cartridges. Sterility of the insertion tool may be accomplished by standard surgical instrument autoclave or gas sterilization processes. Alternatively, avoidance of cross-contamination of the sterile cartridge or sterile surgical field by a non-sterile insertion tool may be accomplished through the use of prophylactic devices made of latex or other similar material, as previously described. Other alternative embodiments previously references of FIGS. 7a and 7b would be similarly employed.

Figure 8:
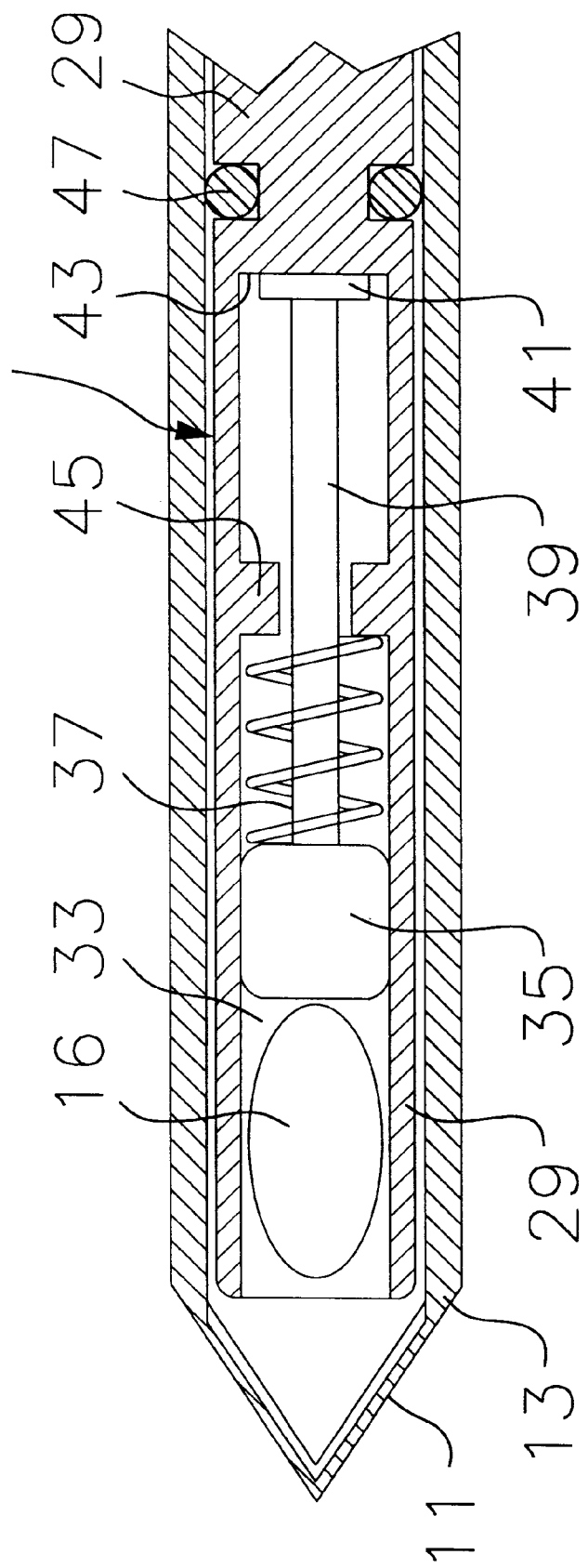
FIG. 8 is a sectional side view of a cartridge having a multi-component assist plug.

Another alternative cartridge 10 according to the invention is shown in FIG. 8. The assist plug 28 is formed of an outer component 29 and an inner component 35. The outer component 29 preferably extends distal the implant 16 and has a hollow interior region 33 that surrounds the implant. The inner component 35 is a slip fit within the proximal end of the hollow interior region 33 of the outer component 29 with at least a portion of the outer component extending proximal the proximal end of the inner component. A compression spring 37, such as a coil spring, is mounted between the inner component 35 and the outer component 29 so that distal movement of the outer component relative to the inner component compresses the spring. Preferably, the inner component 35 has at least one proximal-facing surface in contact with a distally-facing surface of the outer component 29 when the implant 16 is in place as shown, so that distal movement of the outer component results in corresponding distal movement of the inner component. Any other suitable means for moving the inner component distally with the outer component could also be provided.

More specifically, as shown in the depicted embodiment, the inner component 35 includes a rod 39 terminating at its proximal end in a shoulder 41 that is in contact with an inner surface 43 of the outer component 29 so that distal movement of the outer component results in distal movement of the inner component. The spring 37 is mounted in surrounding relation to the rod 39. The outer component 29 includes a circumferential ridge 45 extending into the hollow interior region 33 in contact with the proximal end of the spring 37. The circumferential ridge 45 is sized to prevent the shoulder 41 from moving distally past the ridge. Any other mechanism for preventing the inner component 35 from completely exiting the cartridge could also be provided.

The outer component 29 is fixedly attached at its proximal end to the distal end of the plunger when the cartridge is integral with the insertion tool. Alternatively, when the insertion tool is a separate component and attached to the cartridge, the plunger of the insertion tool engages with the outer component. A sealing means is provided to maintain the sterile seal of the cartridge. In the depicted embodiment, the sealing means comprises an O-ring 47, although any other suitable mechanism known in the art for sealing the cartridge may also be employed. Other means for moving the outer component distally and proximally within the cartridge while maintaining a sealed cartridge could also be provided.

In use, as the plunger is urged distally, the outer component 29 moves distally, pushing open the tip section 11. The outer component 29 and the inner component 35 moving distally together carry the implant out the distal end of the tip section. The outer component 29 can then be withdrawn proximally back into the cartridge by pulling the plunger proximally. The spring 37, or other comparable biasing means, maintains the position of the inner component 35 until the implant is completely uncovered by the outer component 29 to prevent unintentional withdrawal of the implant from the implantation site. The shoulder 41 prevents the inner component from completely exiting the cartridge and being left behind with the implant. Any other means for preventing the inner component from separating from the outer component upon proximal movement of the outer component could also be provided. This embodiment is particularly suitable for an implant made of a solid but weak material that might otherwise be crushed or deformed by the ejection force of the plunger.

Figure 9:
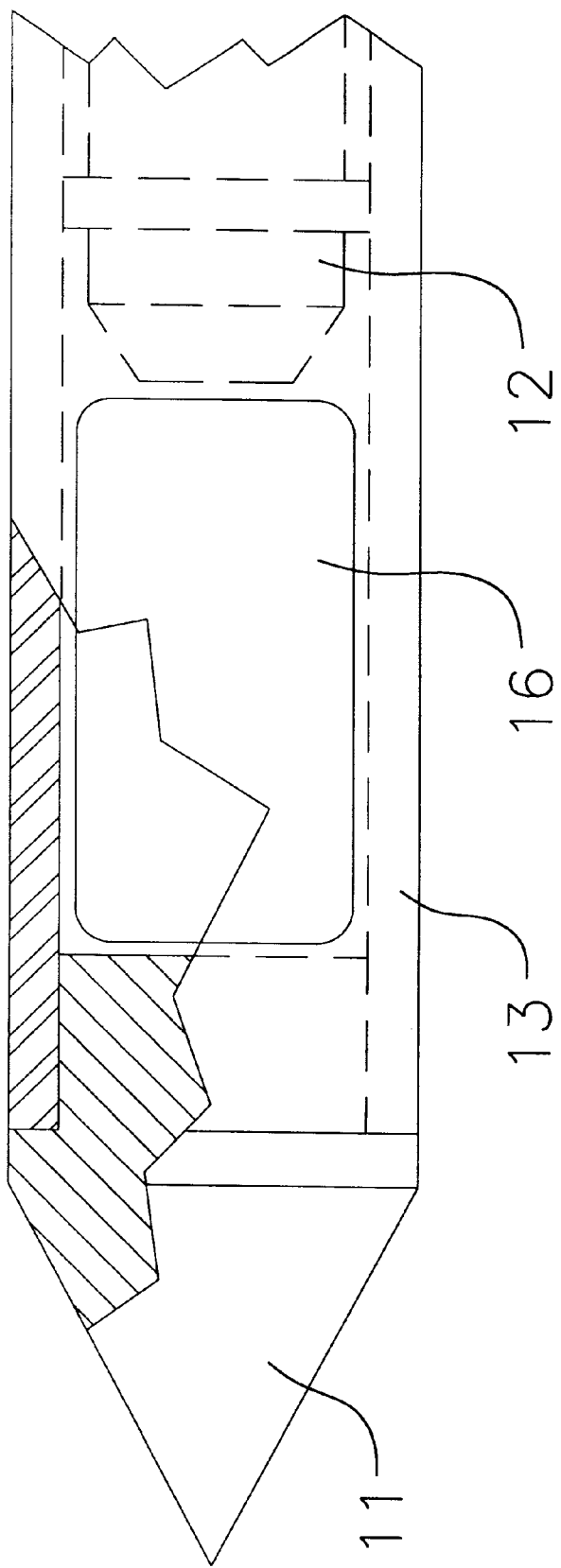
FIG. 9 is a partial sectional side view of an insertion device having a push-out tip section.

In an alternative embodiment, as shown in FIG. 9, the tip section 11 is in the form of a plug made of a dissolvable biocompatible material, such as suture-grade collagen, a polylactic polymer, or a polyglycolic polymer. The tip section 11 is removably attached to the distal end of the cartridge body 13 so that, when the piston 12 urges the implant(s) 16 against the tip section, the tip section slips out of engagement with the cartridge. The tip section then remains in the body with the implant(s). The tip section 11 can be removably attached to the cartridge body 13 by any suitable means, such as a light interference fit or with a coating or membrane, as discussed above. The tip section can then be absorbed by the body. Alternatively, if the nature of the treatment is such that the one or more implants are permanent or intended to be removed surgically at a later time, the tip section can be made of a permanent biocompatible material. The tip section could then be either retrieved with the implant(s) or left implanted indefinitely. If desired, the tip section can be made of the implant material to replace or augment the implant(s). In the instance where the tip section comprises the implant, the plunger (or piston, if used) will directly contact the tip section and push the tip section (implant) off the distal end of the cartridge into the body.

Figure 10:
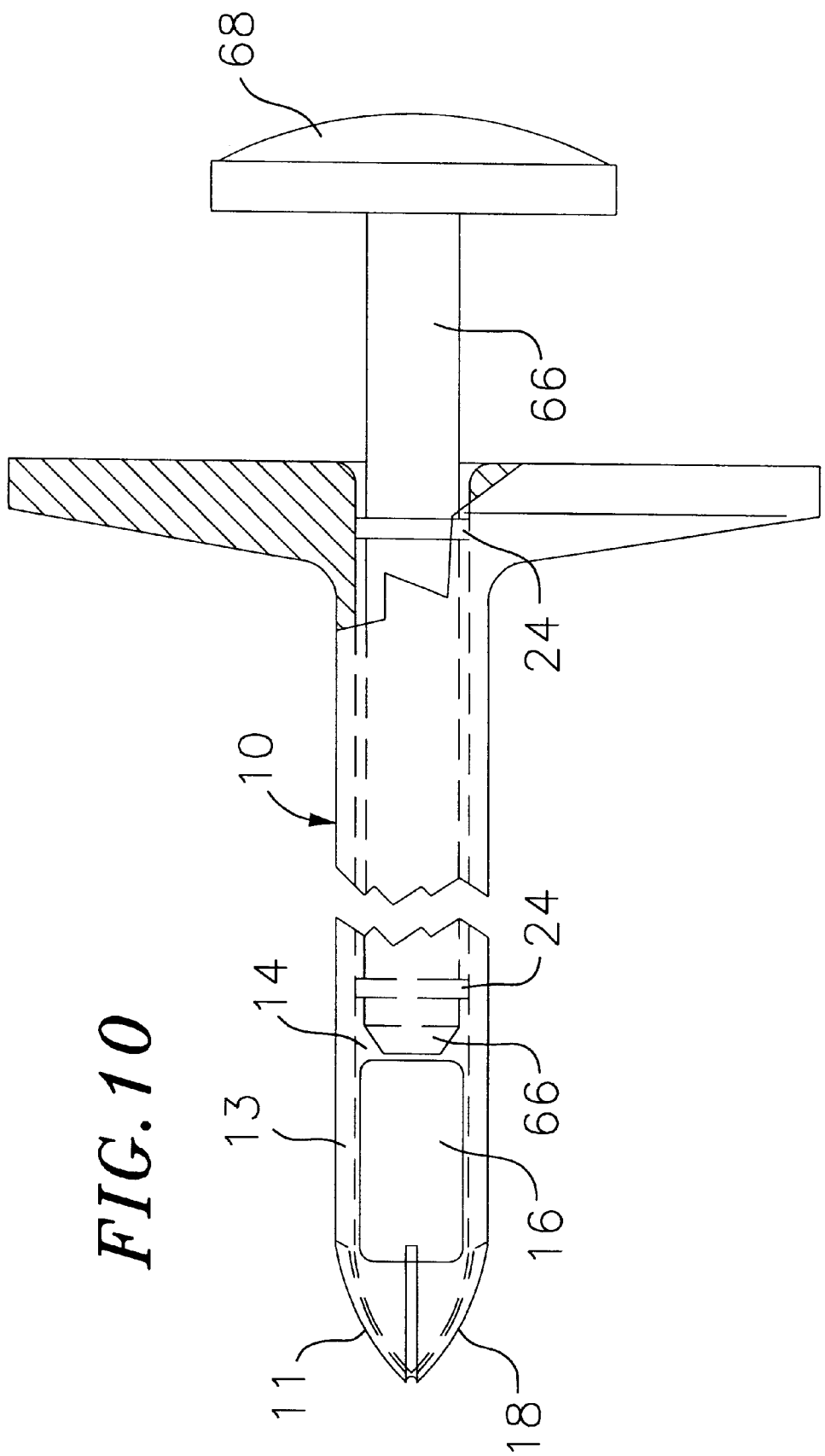
FIG. 10 is a partial sectional side view of an integral insertion device having a cartridge and plunger.

In another embodiment, the invention is directed to an insertion device comprising a cartridge integrated with an insertion tool. Such an insertion device is depicted in FIG. 10. Similar to the embodiments described above, the cartridge 10 comprises a substantially cylindrical body 13 and an internal bore 14 extending therethrough. One or more implants 16 are contained within the bore 14. The pressure-activated self-opening tip section 11 is located at the distal end of the cartridge 10 and has a generally pointed shape and multiple frangible segments 18. A plunger is provided at the proximal end of the insertion device. The plunger comprises a plunger rod 66 having a thumb knob 68 at its proximal end. The plunger rod 66 extends through the internal bore 14 and engages the implant(s) 16. Accordingly, in this embodiment, it may be unnecessary to include a piston 12 (or closure plug) in the cartridge because this function can be provided by suitable features of the plunger rod 66, such as the sealing ribs 24. To facilitate convenient handling of this insertion device, finger tabs and an enlarged plunger proximal end thumb pad are provided and proportioned to achieve a comfortable fit for an average adult hand.

In yet another embodiment, the invention is directed to an integral insertion device useful for vascular implant delivery, as shown in FIGS. 11a and 11b. The insertion device comprises an elongated flexible cartridge 10 having an internal bore 14 extending therethrough. The flexible cartridge can be made of any suitable material, such as polyethylene or polypropylene. One or more implants are contained within the bore 14. A blunt, non-piercing tip section 11 is provided at the distal end of the cartridge and is preferably made of a surgical purity plastic polymer, such as polypropylene, polystyrene or an acrylic polymer. The tip section 11 has a plurality of frangible segments 18, as generally described above. Any of the above-described mechanisms for reinforcing the frangible segments can be incorporated into this embodiment. A plunger is provided at the proximal end of the insertion device. The plunger comprises an elongated, flexible plunger rod 66 having a thumb knob 68 at its proximal end. The plunger rod 66 extends through the internal bore 14 and engages the implant (s) 16 for urging the implant(s) out the distal end of the cartridge and may incorporate suitable sealing means, similar to the embodiment described above for FIG. 10.

Those skilled in the art will recognize alternative approaches for providing gripping features and plunger actuation means in the insertion tool design, such as a piston grip and/or squeeze-action handle, in combination with the novel aspects of the present insertion tool or integral insertion device described above.

The present invention is particularly suitable for insertion of time release drug implants. However, the invention can also be used for insertion of other types of human and animal medical and non-medical implants. As used herein, implants includes, but is not limited to, controlled release drugs and gene therapy implants, various implantable bone and tissue filler and adhesive materials in paste and semi-solid forms, stents, radionuclide seeds, and micro-electronic and nano-mechanical chip implants, and combinations of micro-implants and implantable materials. As would be recognized by one skilled in the art, new implants are constantly being developed that could also be used in connection with the present inventive apparatus and method.

Having now described the invention in detail as required by the patent statutes, those skilled in the art will recognize modifications and substitutions to the embodiments disclosed in this specification. Such modifications and substitutions are within the scope and intent of the present invention as defined in the following claims.

What is claimed is:

1. An apparatus for introducing an implant into tissue comprising:

a cartridge having proximal and distal ends, inner and outer surfaces, and a central bore extending therethrough having proximal and distal ends;

an implant having proximal and distal ends within the central bore;

a piston proximal to the implant and slidably maintained within the bore, whereby, during operation, the piston moves distally through the bore and urges the implant distally through the bore; and an openable tip section at the distal end of the cartridge completely enclosing the distal end of the bore and having inner and outer surfaces;

wherein, in use, when the piston is moved distally to urge the implant distally, the bore is completely enclosed until the tip section is opened.

2. An apparatus according to claim 1, wherein the tip section is segmented or frangible into a plurality of segments under pressure from the distal end of the implant, thereby allowing the implant to emerge from the cartridge.

3. An apparatus according to claim 2, wherein the tip section includes means for inducing stress fracture of the tip to create the plurality of frangible segments.

4. An apparatus according to claim 2, further comprising reinforcement means extending from the cartridge body to the segments of the tip section to prevent separation of the segments from the tip section subsequent to fracture.

5. An apparatus according to claim 1, wherein the tip section is made of a biocompatible material and is removably attached to the cartridge.

6. An apparatus according to claim 2, wherein the junction between the tip section and the cartridge is covered with a coating that reinforces the junction to prevent separation of the segments from the tip section.

7. An apparatus according to claim 6, wherein the coating covers at least a portion of the outer surface of the cartridge and at least a portion of the outer surface of the tip section.

8. An apparatus according to claim 1, wherein the piston is in contact with and maintains a seal with the inner surface of the cartridge.

9. An apparatus according to claim 1, wherein the openable tip section is pressure-activated.

10. An apparatus according to claim 1, further comprising an assist plug having proximal and distal ends within the bore, wherein the distal end of the assist plug is in contact with the inner surface of the tip section.

11. An apparatus according to claim 10, wherein the proximal end of the assist plug is in contact with the distal end of the implant.

12. An apparatus according to claim 10, wherein a portion of the assist plug is contained within the implant.

13. An apparatus according to claim 12, wherein the proximal end of the assist plug is in contact with the piston.

14. An apparatus according to claim 12, wherein the proximal end of the assist plug is fixedly attached to the piston.

15. An apparatus according to claim 10, wherein the assist plug is made of a biocompatible material.

16. An apparatus according to claim 10, wherein at least a portion of the implant is contained within the assist plug.

17. An apparatus according to claim 10, wherein the assist plug comprises:
- an outer component having a hollow interior region containing at least a portion of the implant;
- an inner component within the hollow interior region proximal the implant;
- a compression spring mounted between the inner component and outer component;
- means for moving the outer component distally and proximally within the cartridge;
- means for moving the inner component distally with the outer component; and
- means for preventing the inner component from separating from the outer component upon proximal movement of the outer component;

whereby, in operation, distal movement of the outer component results in distal movement of the inner component and implant so that the implant is carried outside of the bore, and the spring maintains the position of the inner component upon proximal movement of the outer component until the implant is uncovered by the outer component to prevent unintentional withdrawal of the implant back into the cartridge.

18. An apparatus according to claim 17, wherein the means for moving the inner component distally with the outer component comprises a proximally-facing surface of the inner component in contact with a distally-facing surface of the outer component.

19. An apparatus according to claim 17, wherein the means for preventing the inner component from separating from the outer component comprises:

- a circumferential ridge attached to the outer component and extending within the hollow interior region; and
- an inner component including a rod extending within the circumferential ridge and a shoulder proximal the ridge that is too large to pass by the ridge.

20. An apparatus according to claim 1, further comprising a plunger at the proximal end of the cartridge for pushing the piston distally through the bore.

21. An apparatus according to claim 1, wherein the cartridge is made of a flexible material.

22. An apparatus according to claim 1, wherein the tip section has a blunt, non-piercing distal end.

23. An apparatus according to claim 1, wherein the cartridge is made of a flexible material and the tip section has a blunt, non-piercing distal end, and further comprising a plunger at the proximal end of the cartridge for pushing the piston distally through bore.

24. An apparatus according to claim 1, wherein the implant is selected from the group consisting of time-release drug and gene therapy implants, implantable bone and tissue filler and adhesive materials in paste and semi-solid forms, stents, radionuclide seeds, micro-electronic and nano-mechanical chip implants, and combinations thereof.

25. An apparatus according to claim 1, comprising a plurality of implants within the bore.

26. An apparatus for introducing an implant into tissue comprising:
- a cartridge having proximal and distal ends, inner and outer surfaces, and a central bore extending therethrough having proximal and distal ends;
- an implant having proximal and distal ends within the central bore;
- a piston at the proximal end of the cartridge slidably maintained within the bore that is in contact with and maintains a seal with the inner surface of the cartridge, whereby, during operation, the piston moves distally through the bore and urges the implant distally through the bore;
- a pressure-activated tip section at the distal end of the cartridge completely enclosing the distal end of the bore and having inner and outer surfaces, the tip section being segmented or frangible into a plurality of segments under pressure from the distal end of the implant and including means for inducing stress fracture of the tip to create the plurality of frangible segments; and
- reinforcement means extending from the cartridge body to the segments of the tip section to prevent separation of the segments from the tip section subsequent to fracture;
- wherein, in use, when the piston is moved distally to urge the implant distally, the bore is completely enclosed until the tip section is fractured.

27. An apparatus according to claim 26, further comprising an assist plug made of a biocompatible material having proximal and distal ends within the bore, wherein the distal end of the assist plug is in contact with the inner surface of the tip section and the proximal end of the assist plug is in contact with the distal end of the implant.

28. A system for introducing an implant into tissue comprising:
- an apparatus according to claim 1; and
- an insertion tool for urging the piston distally through the bore.

29. A system according to claim 28, wherein the insertion tool comprises:
- means for attaching the tool to the cartridge; and
- means for distally moving the piston.

30. A system according to claim 29, wherein the proximal end of the plunger is within the bore when the distal end of the implant is within the bore.

31. A system according to claim 28, wherein the insertion tool comprises means for removably attaching the tool to the cartridge.

32. A system according to claim 28, wherein the insertion tool comprises means for fixedly attaching the tool to the cartridge.

33. A system according to claim 28, wherein the insertion tool is maintained within a prophylactic covering.

34. A method for introducing an implant into tissue, comprising:
- providing an apparatus as recited in claim 1;
- inserting at least a portion of the distal end of the cartridge into the tissue;
- moving the piston distally through the bore, thereby urging the implant distally through the bore;
- exerting pressure on the tip section with the implant to permit the implant to open the tip section and exit the bore.

35. A method according to claim 34, wherein the distal end of the piston is in direct contact with the proximal end of the implant.

36. A method according to claim 34, wherein the distal end of the implant is in direct contact with the inner surface of the tip section.

37. A method according to claim 34, wherein the apparatus further comprises an assist plug in contact with the implant and with the inner surface of the tip section.

38. A method according to claim 34, wherein the implant is introduced into a surgically-accessed vessel.

39. A method according to claim 34, wherein the implant is introduced into a natural body orifice.

40. A method according to claim 34, wherein the implant is introduced subcutaneously.

41. A method according to claim 34, wherein the implant is selected from the group consisting of time-release drug and gene therapy implants, implantable bone and tissue filler and adhesive materials in paste and semi-solid forms, stents, radionuclide seeds, micro-electronic and nano-mechanical chip implants, and combinations thereof.

* * * * *